United States Patent [19] [11] 4,227,016
Herman et al. [45] Oct. 7, 1980

[54] PROCESS FOR MANUFACTURING α-CHLOROARYLACETIC ACIDS

[75] Inventors: Emmanuel Herman, Sarcelles, France; Helmut Diery, Kelkheim, Fed. Rep. of Germany; Michel Soreau, Montmorency; Yani Christidis, Paris, both of France

[73] Assignee: Hoechst France, Puteaux, France

[21] Appl. No.: 865,285

[22] Filed: Dec. 28, 1977

[30] Foreign Application Priority Data

Dec. 30, 1976 [FR] France ................................ 76 39628

[51] Int. Cl.$^3$ .............................................. C07C 57/58
[52] U.S. Cl. ................................... 562/465; 562/492; 562/488; 562/478; 562/496
[58] Field of Search .......... 260/515 A, 521 H, 520 R; 562/496, 492, 478, 488, 489, 465

[56] References Cited

U.S. PATENT DOCUMENTS

| | | | |
|---|---|---|---|
| 2,876,255 | 3/1959 | Johnston | 562/496 |
| 3,634,504 | 1/1972 | Young | 562/496 |
| 3,637,828 | 1/1972 | Holtschmidt et al. | 562/470 |
| 4,008,269 | 2/1977 | Diamond et al. | 260/515 A |

FOREIGN PATENT DOCUMENTS 1377243 12/1974 United Kingdom ..................... 562/470

OTHER PUBLICATIONS

Quelet, Bull. Soc. Chim. 1, 196–205 (1940). (CA, 1940, 5425).
Mar., *Advanced Organic Chemistry: Reactions Mechanisms and Structure*, pp. 424 and 421, (1968).

*Primary Examiner*—Jane S. Myers
*Attorney, Agent, or Firm*—Karl W. Flocks

[57] ABSTRACT

Glyoxylic acid and hydrochloric acid are reacted with an aromatic compound having at least one substituent group selected from among the alkyl, aryl, hydroxy, alkoxy and aryloxy groups. The glyoxylic acid is used in a concentration comprised between 60 and 100% and the hydrochloric acid is used in as concentrated an aqueous solution as possible, e.g. in an organic solvent medium such as acetic acid. An acid catalyst such as zinc chloride may be used. The reaction may be carried out under pressure. The products are useful in various syntheses e.g. to produce amino acids or arylacetic acids with medicinal uses.

19 Claims, No Drawings

PROCESS FOR MANUFACTURING α-CHLOROARYLACETIC ACIDS

BACKGROUND OF THE INVENTION

1. Field of the Invention

The present invention relates to a process for the manufacture of α-chloroarylacetic acids and, to the novel α-chloroarylacetic acids produced by this process.

2. Description of the Prior Art

The simplest of the α-chloroarylacetic acids, namely α-chlorophenylacetic acid, has long been known. The method most currently used for preparing it consists of reacting thionyl chloride with ethyl mandelate, which reaction is followed by transesterification by acetic acid of the ester obtained (Organic Synthesis IV p. 169-172). By a similar process a certain number of α-chloroarylacetic acids substituted on the nucleus, such as α-chloro(-methyl-4) phenylacetic acid and α-chlorobiphenylacetic acid, have been prepared.

Another process for the preparation of α-chloroarylacetic acids consists of reacting ethylchloroethoxyacetate with an aromatic compound. This method is particularly interesting when the aromatic compound is a phenol ether (R. QUELET and J. GAVARRET—Bull.Soc.Chim. 1950 p. 1075-8).

The drawback of these two methods is that they necessitate the prior preparation of an intermediate compound which is not currently available commercially: an α-hydroxyarylacetic compound for the first, ethylchloroethyoxyacetate for the second, and that they are relatively complicated.

It is an object of the present invention to provide a process for the preparation of α-chloroarylacetic acids which overcomes these drawbacks.

It is another object to provide α-chloroarylacetic acids which are novel.

Other objects and advantages will become apparent from the description which follows.

GENERAL DESCRIPTION OF THE INVENTION

It has now been found that it is possible to prepare α-chloroarylacetic acids directly and simply by the action of glyoxylic acid and hydrochloric acid on the corresponding aromatic compounds.

The overall reaction may be represented in the following manner in the case of toluene, for example:

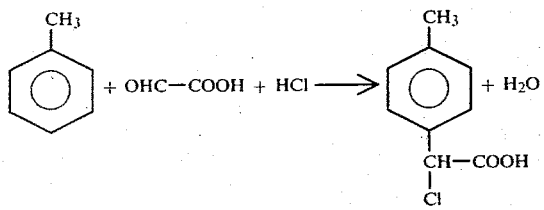

The process of manufacture according to the invention is usable in principle with all aromatic compounds having at least one free position capable of fixing a —CHCl—COOH group. However in fact, the fixing of such a group being much influenced by the other substituents present on the aromatic nucleus, the east of obtaining α-chloroarylacetic acids varies substantially according to the substituents already present on the nucleus. Modification of the operational conditions permits compensation for these differences in reactivity to a certain extent.

The aromatic nuclei including electron-donor substituents such as as alkyl, hydroxy, or alkoxy groups orient the fixing of the —CHCl—COOH group in the para position and to lesser degree in the ortho position. With aromatic compounds including a hydroxyl or alkoxy group, which are particularly reactive, reaction does not generally stop at the fixing of the —CHCl—COOH group and it forms diarylacetic compounds. In the same way, aromatic nuclei including an aryl or aryloxy substituent show a reactivity permitting use of the invention. On the other hand, nuclei including substituents having an electron-attractor character such as carboxyl, nitro, or halogen groups, fix the —CHCl—COOH group with difficulty. Nuclei including both an electron-donor and an electron-attractor group can fix a —CHCl—COOH group.

Aromatic compounds usable in the process according to the invention are hence preferably those including on the nucleus an alkyl and/or aryl and/or hydroxyl and/or alkoxy and/or aryloxy group, such as for example, toluene, the xylenes, mesitylene, pseudocumene, ditertiobutyl-2,6-phenol methoxy-4 toluene, biphenyl oxide, as well as biphenyl itself.

Generally, the reaction is carried out in a concentrated aqueous hydrochloric solution or for aromatic compounds which are poorly reactive, in an organic solvent medium such as acetic acid, if necessary in the presence of an acid catalyst such as zinc chloride, at temperatures ranging up to boiling temperature or even under pressure.

The reaction taking place with the elimination of water, it is advantageous to use glyoxylic acid containing the minimum of water, that is to say, glyoxylic acid of a concentration between 60 and 100%, in particular 80%. To increase the concentration of HCl it is generally advantageous to pass a current of gaseous HCl into the reaction mixture during the reaction.

The proportions of the reactants vary according to the reactivity of the aromatic compound; It is sometimes advantageous to use an excess of glyoxylic acid and a very large excess of hydrochloric acid. The temperature and the reaction times are also a function of the reactivity of the aromatic compound.

Due to the fact of the ease of hydrolysis of the α-chloroacetic acids and of the necessity to dilute the reaction medium with water in order to precipitate the compound formed when operating in an acetic medium, the product obtained sometimes contains, as an impurity, α-hydroxyarylacetic acids. In the same way α-chloroacetic acids obtained from phenols or from their ethers may contain, as an impurity, bisarylacetic acids.

The α-chloroarylacetic acids obtained according to the process of the invention are intermediate in various syntheses, notably of amino acids by replacement of the Cl by a —NH₂ group by means of ammonia. They are hydrolysed in contact with water giving the corresponding α-hydroxyarylacetic acids; they can also be reduced to arylacetic acids which frequently possess analgesic or anti-inflammatory properties.

α-chlorobiphenylacetic acid has also been recommended in anti-inflammatory compositions (British Pat. No. 1,030,756).

DESCRIPTION OF PREFERRED EMBODIMENTS

The following examples are given purely by way of non-limiting illustration.

EXAMPLE 1

Gaseous hydrochloric acid is bubbled for 18 hours at 60° C. into a solution containing 37 g (0.4 mole) of 80% glyoxylic acid, 34.5 g (0.375 mole) of toluene, 30 g of fused zinc chloride and 200 ml of glacial acetic acid. After cooling, it is treated with a normal solution of hydrochloric acid in order to separate the water soluble products. After decantation, the lower layer was taken up with 500 ml of heptane A, and it was left to crystallise at 0° C. In this manner 9.75 g of crude product was obtained (yield 14%). The NMR spectrum of this product is compatible with the structure of α-chloro(methyl-4)phenylacetic acid. After re-crystallisation in heptane A the product titrated: at:
—COOH: 102% of theory
—Cl: 98% of theory

EXAMPLE 2

A solution containing 310 g of 80% glyoxylic acid (5.5 moles), 330 g of fused and ground zinc chloride, 875 g (5.5 moles) of metaxylene and 1650 ml of hydrochloric acid (d=1.18) was brought to 60° C., bubbling gaseous HCl therethrough. After 6 hours at 60° C., the precipitate formed was filtered off, it was washed with 500 ml of approximately normal hydrochloric acid; the crude product was re-crystallised in 750 ml of benzene and then re-formed into a paste in twice 750 ml of heptane A. After drying, 509 g of dry product (yield 46.6%) was obtained. After another re-crystallisation in benzene, the white product obtained had the following characteristics:

NMR spectrum in accordance with the structure provided for α-chloro(dimethyl-2,4)phenylacetic acid.
MP (capillary tube)=106°–107° C.
C %=59.86–60.07: (theory 60.45)
H %=5.58–5.59: (theory 5.58)
Cl %=17.9: (theory 17.87)

EXAMPLE 3

A trial also carried out with metaxylene, using an excess of 30% glyoxylic acid, 100 g of zinc chloride per molecule of metaxylene, 5 times the theoretical amount of HCl in the form of a 36% solution with bubbling of gaseous HCl throughout the operation, gave for a reaction time of 5 hours, a yield of 60% of crude α-chloro(-dimethyl-2,4) phenylacetic acid.

EXAMPLE 4

A solution containing 122 g (1 mole) of mesitylene, 116 g (1.25 mole) of 80% glyoxylic acid, 25 g of fused zinc chloride and 205 g of 36% hydrochloric acid was brought to 60° C. and was kept at this point for 5 hours with bubbling of gaseous HCl. After cooling, the precipitate was separated, washed with hydrochloric acid and dried (yield of crude product 55%). After re-crystallisation in benzene (yield 80%) an α-chloro(trimethyl-2,4,6) phenylacetic acid melting at 144°–145° C. was obtained.
Acidimetry: 97% of theory
Cl %=16.2: (theory 16.5)

EXAMPLE 5

A mixture of 122 g (1 mole) of pseudocumene, 120 g (1.3 mole) of 80% glyoxylic acid, 60 g of fused zinc chloride and 102 g of 36% hydrochloric acid was brought to 60° C. for four hours with bubbling of gaseous hydrochloric acid. After cooling, the precipitate was separated, washed with aqueous hydrochloric acid and dried (yield 80%). The crude product melted at 122° C. and titrated at 14.5% of chlorine (theory 15.5%). After re-crystallisation from benzene, the α-chloro(trimethyl-2,3,5)phenylacetic acid obtained titrated at 15.8% of chlorine (theory 16.5%).

EXAMPLE 6

A mixture of 57.8 g (0.375 mole) of biphenyl, 55.6 g (0.6 mole) of 80% glyoxylic acid, 45 g of fused zinc chloride and 150 ml of glacial acetic acid were kept for 12 hours at 60° C. under a current of gaseous HCl. After cooling it was precipitated in 1.300 liters of normal hydrochloric acid at 5° C. The precipitate was taken up at 60° C. in 500 ml of toluene. It was crystallised by adding 1 liter of heptane A, and 29.3 g of crude product (yield 29.5%) was collected. The NMR spectrum of this product was compatible with the structure of α-chlorobiphenylacetic acid.

After re-crystallisation the product titrated:
—COOH about 100% of theory
—Cl about 100% of theory

EXAMPLE 7

A mixture of 389.4 g (2.5 moles) of biphenyl, 694 g (7.5 moles) of 80% glyoxylic acid, 300 g of anhydrous zinc chloride, 2000 ml of pure glacial acetic acid and 548 g of 100% hydrochloric acid was kept for 12 hours at 60° C. with stirring and under a pressure of about 4 bars. After cooling, an aliquot part of the mixture, namely 617 g, was precipitated in water. The precipitate was washed with water and then redissolved in 600 ml of chlorobenzene. After separation of the aqueous layer, the chlorobenzene solution was precipitated by 600 ml of heptane. One half of the precipitate obtained was dried at 60° C. under vacuum: 21.6 g of the crude product, namely a yield of 41% was obtained. The other half was re-crystallised in 1.5 l of heptane; 14.4 g of re-crystallised product, namely a yield of 28%, was obtained.

The crude α-chlorobiphenylacetic acid melted at 125°–130° C., titrated about 100% of the theoretical Cl. The re-crystallised product melted at 135°–138° C.

EXAMPLE 8

A mixture of 464 g (3 moles) of biphenyl, 925 g (10 moles) of 80% glyoxylic acid, 300 g of zinc chloride, 2000 ml of glacial acetic acid and 760 g of 100% hydrochloric acid were kept for 2 hours at 70°–75° C. and then for 8 hours at 80° C. with stirring, in an enamelled autoclave.

At the end of the operation the pressure reached 9 bars. An aliquot part of the mixture, namely 419 g, was precipitated in water and washed. The moist precipitate was taken up with hot chlorobenzene; the water was separated and the product was re-crystallised by cooling the chlorobenzene solution. 39 g of dry product corresponding to the disubstituted derivative of biphenyl (namely biphenyl bis(α-chloroacetic)-4,4') acid, being a yield of 40% with respect to the biphenyl, was obtained.

The crude product was purified by stirring with hot heptane which dissolved the monosubstituted derivative. The yield of purified product: 34% with respect to the biphenyl. The purified product melted at 180°–182° C. and the —COOH titrated at about 100% of theory.

EXAMPLE 9

Gaseous HCl was bubbled for 30 minutes at 40° C. into a solution of 92.5 g (1 mole) of 80% glyoxylic acid in 200 ml of hydrochloric acid (d=1.18). In 2 h 30 at 20° C., 51.5 g (0.25 mole) of ditertiobutyl-2,6 phenol diluted to 100 ml with glacial acetic acid was then added with the bubbling of gaseous HCl. It was then left to react for 2 hours and then cooled to 5° C. It was filtered, washed with about N HCl, reformed into paste with heptane (3 times 100 ml). 27.85 g of crude product (yield 37%) was obtained whose NMR spectrum was compatible with the structure of α-chloro (ditertiobutyl-3,5,hydroxy-4) phenylacetic acid.

EXAMPLE 10

A solution of 92.5 g (1 mole) of 80% glyoxylic acid in 200 ml of aqueous hydrochloric acid (d=1.18) was saturated with gaseous HCl. The temperature reached 30° C. At this temperature and with the bubbling of HCl, 30.6 g (0.25 mole) of methoxy-4 toluene was run in 3 h 30. It was allowed to react for 2 hours and then cooled to 10° C. before filtration. The solid was washed with water and dried. 44.7 g of α-chloro(methoxy-2, methyl-5)phenylacetic acid (yield 83%) was obtained.
—COOH: about 100% of theory
—Cl: 96.6% of theory.

EXAMPLE 11

A solution of 92.5 g (1 mole) of 80% glyoxylic acid and 30 g of fused and ground zinc chloride in 75 ml of glacial acetic acid was saturated with gaseous HCl. 42.5 g (0.25 mole) of biphenyl oxide was then run in. It was kept at 50° C. with the bubbling of HCl for 6 hours. After cooling, the solution was treated with twice 1 liter of water and extracted twice with 250 ml of methylene chloride; by evaporation of the methylene chloride about 64 g of crude resin was obtained, namely a yield of 70% of a crude product whose NMR spectrum was compatible with the structure of bis (α-chloroacetic)-4,4' diphenyloxide acid.

It is self-evident that the present invention has only been described in a purely indicative and in no way limiting manner and that any useful modifications could be introduced therein without departing from its scope, as defined by the appended claims.

We claim:

1. Process for producing alphachloroarylacetic acids comprising mixing glyoxylic acid and hydrochloric acid and then reacting with an aromatic compound comprising a benzene ring and having thereon at least one substituent group selected from the group consisting of alkyl, aryl, hydroxy, alkoxy and aryloxy, and having at least one free position capable of fixing a —CHCl—COOH group.

2. Process according to claim 1, wherein the glyoxylic acid has a concentration between 60 and 100%.

3. Process according to claim 2, wherein said glyoxylic acid is 80% concentrated acid.

4. Process according to claim 1, in which the hydrochloric acid is used in as concentrated an aqueous solution as possible.

5. Process according to claim 1, in which the hydrochloric acid is used in an organic solvent medium.

6. Process according to claim 5, in which said organic solvent is acetic acid.

7. Process according to claim 1, in which the reaction is carried out in the presence of an acid catalyst.

8. Process according to claim 7, in which said acid catalyst is zinc chloride.

9. Process according to claim 1, in which the reaction is carried out under pressure.

10. Process according to claim 1, in which an excess of glyoxylic acid is used in the reaction.

11. Process according to claim 1, in which an excess of hydrochloric acid is used in the reaction.

12. Process according to claim 1, in which the glyoxylic acid and the hydrochloric acid are reacted with metaxylene to obtain alpha-chloro(dimethyl 2,4) phenylacetic acid.

13. Process according to claim 1, in which the glyoxylic acid and the hydrochloric acid are reacted with mesitylene to obtain alpha-chloro (trimethyl-2,4,6)phenylacetic acid.

14. Process according to claim 1, in which the glyoxylic acid and the hydrochloric acid are reacted with pseudocumene to obtain alpha-chloro(trimethyl-2,3,5)phenylacetic acid.

15. Process according to claim 1, in which the glyoxylic acid and the hydrochloric acid are reacted with biphenyl to obtain biphenyl bis (alpha-chloroacetic)-4,4' acid.

16. Process according to claim 1, in which the glyoxylic acid and the hydrochloric acid are reacted with ditertiobutyl-2,6 phenol to obtain alpha-chloro(-ditertiobutyl-3,5, hydroxy-4) phenylacetic acid.

17. Process according to claim 1, in which the glyoxylic acid and the hydrochloric acid are reacted with methoxy-4 toluene to obtain alpha-chloro (methoxy-2, methyl-5)phenylacetic acid.

18. Process according to claim 1, in which the glyoxylic acid and the hydrochloric acid are reacted with biphenyl oxide to obtain bis(alpha-chloroacetic)-4,4' diphenyloxide acid.

19. A process for producing alpha-chloroarylacetic acids comprising reacting glyoxylic acid and hydrochloric acid with an aromatic compound having at least one free position capable of fixing a —CHCl—COOH group, said aromatic compound being selected from the group consisting of toluene, xylenes, mesitylene, pseudocumene, di-tertiobutyl-2,6-phenol, methoxy-4 toluene, biphenyl oxide and biphenyl.

* * * * *